(12) United States Patent
Yee et al.

(10) Patent No.: US 8,770,198 B2
(45) Date of Patent: Jul. 8, 2014

(54) CONNECTOR

(75) Inventors: Arthur Kin-wai Yee, Pymble (AU);
Benjamin John Hunter, Castle Hill (AU); Christopher Joseph Brunner, Newtown (AU)

(73) Assignee: ResMed Limited, Bella Vista (AU)

( * ) Notice: Subject to any disclaimer, the term of this patent is extended or adjusted under 35 U.S.C. 154(b) by 1421 days.

(21) Appl. No.: 12/448,306

(22) PCT Filed: Dec. 13, 2007

(86) PCT No.: PCT/AU2007/001926
§ 371 (c)(1),
(2), (4) Date: Jun. 17, 2009

(87) PCT Pub. No.: WO2008/074058
PCT Pub. Date: Jun. 26, 2008

(65) Prior Publication Data
US 2009/0260629 A1    Oct. 22, 2009

Related U.S. Application Data

(60) Provisional application No. 60/935,819, filed on Aug. 31, 2007.

(30) Foreign Application Priority Data

Dec. 21, 2006  (AU) ................................ 2006907105
May 15, 2007  (AU) ................................ 2007902567

(51) Int. Cl.
*A63B 21/00*    (2006.01)

(52) U.S. Cl.
USPC ................................ 128/207.18; 128/207.13

(58) Field of Classification Search
USPC ........................... 128/207.13, 203.12, 207.18
See application file for complete search history.

(56) References Cited

U.S. PATENT DOCUMENTS

| | | |
|---|---|---|
| 4,944,310 A | 7/1990 | Sullivan |
| 5,497,765 A | 3/1996 | Praud et al. |
| 5,704,345 A | 1/1998 | Berthon-Jones |
| 6,029,665 A | 2/2000 | Berthon-Jones |
| 6,138,675 A | 10/2000 | Berthon-Jones |
| 6,363,933 B1 | 4/2002 | Berthon-Jones |
| 7,128,069 B2 | 10/2006 | Farrugia et al. |

FOREIGN PATENT DOCUMENTS

| | | |
|---|---|---|
| SU | 839551 | 8/1981 |
| WO | WO 01/19436 | 3/2001 |
| WO | WO 01/19436 A1 * | 3/2001 |
| WO | WO/2005/063323 | 7/2005 |

OTHER PUBLICATIONS

International Search Report for PCT/AU2007/001926, dated Feb. 4, 2008.

* cited by examiner

*Primary Examiner* — Jerome W Donnelly
(74) *Attorney, Agent, or Firm* — Nixon & Vanderhye P.C.

(57) ABSTRACT

A connector includes a main conduit and a gas conduit. The main conduit includes an inlet portion and an outlet portion that form a passage for supply of a first gas in a forward direction. The inlet portion is adapted to receive a supply of the first gas and deliver the first gas to the outlet portion. The gas conduit has a first end and a second end that form a second passage for supply of a second gas. The first end of the gas conduit is adapted to connect to a second gas supply, and the second end is adjacent the outlet portion of the main conduit and delivers the second gas into the main conduit such that the second gas is directed to flow in a forward direction.

25 Claims, 15 Drawing Sheets

CONNECTOR

CROSS-REFERENCE TO APPLICATIONS

This application is the U.S. national phase of International Application No. PCT/AU2007/001926, filed Dec. 13, 2007, which designated the U.S. and claims the benefit of Australian Provisional Application Nos. AU 2006907105, filed 21 Dec. 2006, and AU 2007902567, filed 15 May 2007, and U.S. Provisional Application No. 60/935,819, filed Aug. 31, 2007, each of which is incorporated herein by reference in its entirety.

FIELD OF THE INVENTION

The present invention relates to a connector for delivery of a supplementary gas, such as oxygen, to a patient using a respiratory ventilation device, particularly a Positive Airway Pressure (PAP) device for ventilatory assistance.

DESCRIPTION OF RELATED ART

Respiratory ventilation devices are used to assist a range of conditions and patient needs. Respiratory ventilation devices include: invasive ventilators and non-invasive ventilators such as Positive Airway Pressure (PAP) devices. PAP devices are used in the treatment of sleep related breathing disorders such as Obstructive Sleep Apnea (OSA). Colin Sullivan was the first to describe the use of nasal Continuous Positive Airway Pressure (CPAP) to treat Obstructive Sleep Apnea (OSA), e.g., see U.S. Pat. No. 4,944,310. OSA is characterised by partial or complete occlusion (i.e., apnea) of the upper airway passage during sleep. OSA sufferers repeatedly choke on their tongue and soft palate throughout the entire sleep period resulting in lowered arterial blood oxygen levels and poor quality of sleep.

Continuous positive airway pressure (CPAP) treatment generally provides a continuous supply of air or breathable gas from a blower to a patient via an air delivery conduit and a patient interface, such as a full-face or nasal mask or nasal prongs. The air or breathable gas is commonly delivered at a pressure of 4 $cmH_2O$ to 28 $cmH_2O$ and acts as a splint to hold the airway open during sleep. However, the pressure required for effective CPAP therapy differs between patients and is generally determined following analysis by a sleep specialist. CPAP therapy has been shown to effectively eliminate both snoring and obstructive sleep apneas. However, some patients complain of discomfort with CPAP therapy.

Another type of CPAP device known as a Bilevel PAP device provides a first pressure during inhalation (commonly termed an IPAP) and a second, lower pressure during exhalation (commonly termed an EPAP). Some patients perceive that the lower pressure during exhalation is more comfortable, at least while they are awake. Examples of these devices include the ResMed VPAP® series, and the Respironics BiPAP® series. Bilevel CPAP devices may be prescribed for patients who are not compliant with single pressure CPAP devices. Another type of therapy mode used in combination with CPAP therapy provides a reduced pressure during expiration to assist the patient when exhaling. See U.S. Pat. No. 7,128,069.

Another form of CPAP therapy can be provided by an automatically adjusting CPAP device such as the ResMed AUTOSET™ SPIRIT™ device. In such devices, the CPAP pressure is automatically increased or decreased in accordance with indications of flow limitation, such as flow flattening, snore, apnea and hypopnea. See U.S. Pat. Nos. 5,704,345; 6,029,665; 6,138,675; and 6,363,933. These patents also describe a method and apparatus for distinguishing between so-called "central" and obstructive apneas. More recently automatically adjusting Bilevel devices have been described, where both the IPAP and the EPAP pressures are capable of being automatically increased or decreased in accordance with indications of flow limitation as described above. See pending patent application WO 2005/063323.

An advantage of an automatically adjusting system is that it provides the patient with an elevated PAP only when required. This means that the patient is spared the discomfort of receiving the highest treatment pressure during the whole treatment session. Furthermore while the treatment pressure required for a particular patient may vary over time a correctly functioning automatic system may obviate the need for the patient to return for a subsequent sleep study to reset the treatment pressure deliver by the PAP device.

Some patients require supplemental gas, such as oxygen, helium, nitrogen or combinations thereof, to be supplied together with the pressurized gas being delivered via the respiratory ventilator or PAP device. Such patients may suffer from chronic lung or heart problems such as chronic obstructive pulmonary disease (COPD), pulmonary fibrosis or heart failure. Other patients may have acute lung problems such as pneumonia and require supplemental gas for a limited time. Supplemental gas may also be required for some patients living or visiting at high altitudes or traveling on an airplane.

A gas adaptor is often used to provide supplementary gas, such as oxygen, to the patient via the air delivery system in a PAP device. Prior art gas adaptors feed the gas at a right angle into the main air path. The supplementary gas entering the main air path is propelled in the direction of the main gas flow when the PAP device is on. However, if the supplementary gas supply is left on when the PAP device is turned off the supplementary gas may flow in either direction presenting a safety risk. Oxygen is generally delivered in a typical range of 2-15 liters/minute. Increasing oxygen levels in some parts of the PAP device can present an increased risk of fire due to the combustion risk when high levels of oxygen are present.

A further type prior art gas adaptor includes an oxygen diverter valve. Such diverter valves are designed to prevent oxygen from flowing back into a PAP device during interruptions in therapy. These devices function by blocking the path back to the PAP device when the device is turned off or a fault occurs such that pressurized air does not flow. These are similar to anti-asphyxia valves commonly used in masks. However, the blocking of the path to the PAP device when the device is turned off means that automatic breath detection systems do not function. For example, the SmartStart™ feature found in the ResMed S8™ CPAP device.

A Venturi oxygen mask is produced by HAFOE to deliver a fixed concentration of oxygen. This mask draws in room air into the stream of oxygen. The air is drawn in and mixed with the oxygen using a Venturi effect. However, this mask is not suitable for CPAP use.

The entire contents of all of the aforesaid patents are incorporated by cross-reference.

SUMMARY OF THE INVENTION

An aspect of the present invention is to provide a connector that improves the delivery of oxygen to a patient using a respiratory system such as a PAP device.

Another aspect of the invention is to provide a connector that directs the gas in a safe and targeted manner into the air path of a PAP device to reduce backflow of oxygen into the device even when the device is off.

In a further aspect of the invention, the connector delivers the gas using a Venturi effect, thus directing the gas to flow in substantially a single direction to prevent backflow of oxygen into PAP device.

Another aspect of the invention relates to a connector comprising a main conduit and a gas conduit. The main conduit having an inlet portion and an outlet portion that form a passage for supply of a first gas in a forward direction, the inlet portion is adapted to receive a supply of the first gas and deliver the first gas to the outlet portion. The gas conduit having a first end and a second end that form a second passage for supply of a second gas, the first end of the gas conduit is adapted to connect to a second gas supply, and the second end is adjacent the outlet portion of the main conduit and delivers the second gas into the main conduit such that the second gas is directed to flow in the forward direction.

Another aspect of the invention relates to a connector adapted to provide supplemental gas to a respiratory system. The connector includes a main conduit and a gas conduit. The main conduit has an inlet portion and an outlet portion that form a passage for supply of a first gas in a forward direction. The inlet portion is adapted to receive a supply of the first gas and deliver the first gas to the outlet portion. The gas conduit has a first end and a second end that form a second passage for supply of a second gas. The first end of the gas is adapted to connect to a second gas supply, and the second end is adjacent the outlet portion of the main conduit and delivers the second gas into the main conduit such that the second gas is directed to flow in a forward direction.

Another aspect of the invention relates to a connector for providing supplemental gas to a respiratory system. The connector includes a main conduit having an inlet portion and an outlet portion that form a first passage for supply of a first gas, and a supplemental conduit having a first end and a second end that form a second passage for supply of a second gas. The second end is positioned and arranged to direct the second gas into a center of the first passage.

Another aspect of the invention relates to a method for treating a patient with chronic lung or heart problems. The method includes delivering pressurized gas to the patient and providing a supplemental gas to the pressurized gas while minimizing additional impedance and/or turbulence due to the introduction of the supplemental gas.

Another aspect of the invention relates to a method for providing supplemental gas to a respiratory system. The method includes delivering pressurized gas along a first passage and providing a supplemental gas to the first passage along a center of the first passage.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF FIGURES

The accompanying drawings facilitate an understanding of the various embodiments of this invention. In such drawings:

FIGS. 6-1 to 6-12 show various views of a connector according to another embodiment of the present invention;

FIG. 7 is a perspective view illustrating a connector attached to a PAP device according to an embodiment of the present invention;

FIGS. 8-1 to 8-2 show various views of a connector according to another embodiment of the present invention;

FIG. 9 is a front view of a connector according to another embodiment of the present invention;

FIGS. 10-1 to 10-2 show various views of a fin for a connector according to an embodiment of the present invention;

FIG. 11-1 illustrates flow through the connector shown in FIGS. 6-1 to 6-12 at high pressure from a PAP device (20 cmH2O) according to an embodiment of the present invention; and FIG. 11-2 illustrates flow through the connector shown in FIGS. 6-1 to 6-12 at high oxygen flow from the gas conduit (15 L/min) according to an embodiment of the present invention.

DETAILED DESCRIPTION OF ILLUSTRATED EMBODIMENTS

Figure 1:
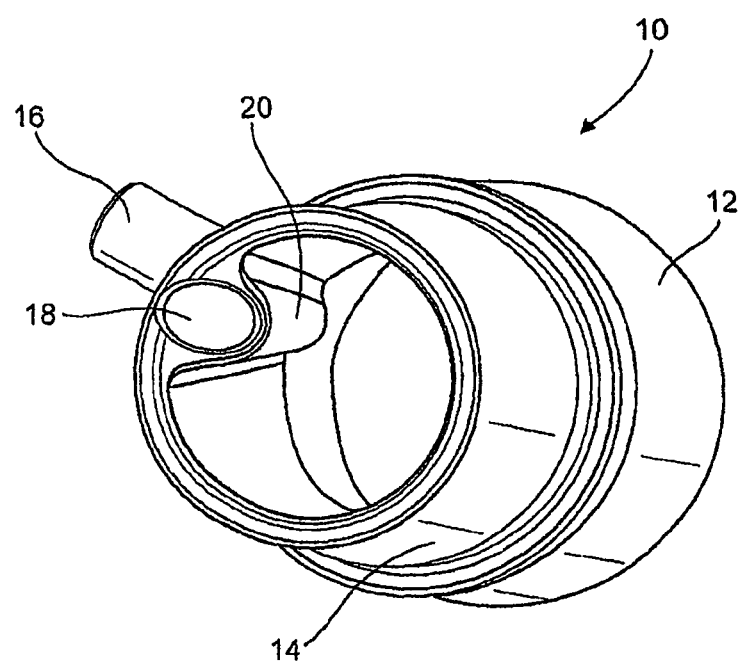
FIG. 1 is a perspective view of a connector according to an embodiment of the invention.
Figure 2:
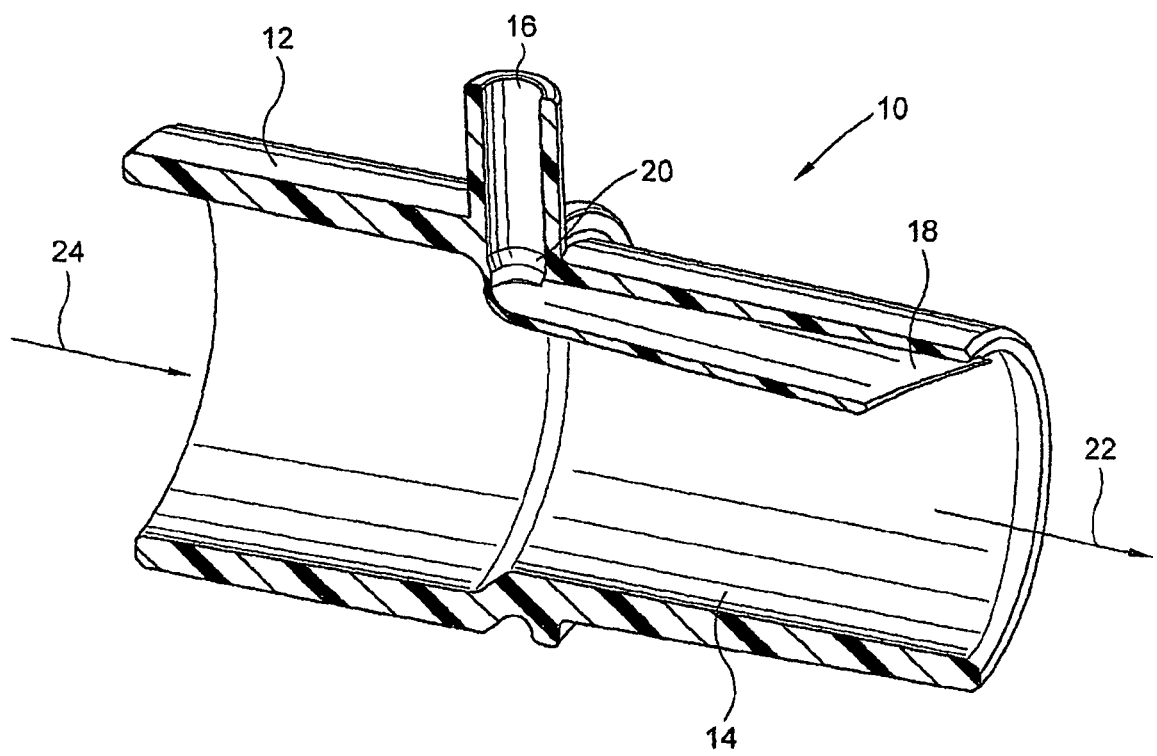
FIG. 2 is a cross section view of the connector of FIG. 1.
Figure 3:
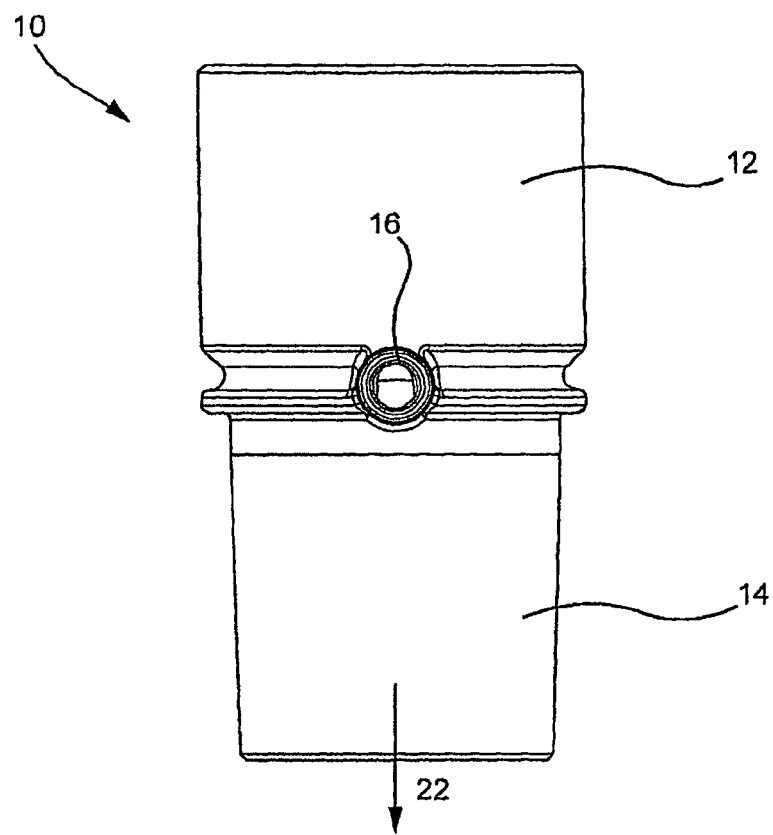
FIG. 3 is a side view of a connector according to an embodiment of the invention.

FIGS. 1-3 show a connector 10 according to an embodiment of the invention. The connector comprises a main conduit having an inlet portion 12 and an outlet portion 14 that form a passage for supply of a first gas. The inlet portion 12 is adapted to receive a supply of a first gas and deliver the first gas to the outlet portion 14 as indicated by arrows 22 and 24. The direction indicated by arrows 22 and 24 is considered the forward direction. The connector further comprises a gas conduit 20 having a first end 16 and a second end 18 that form a second passage for supply of a second gas. The first end 16 is adapted to connect to a second gas supply using any known attachment mechanism.

In one embodiment, the gas conduit 20 has a generally L-shape such that the supplied gas is directed from a substantially vertical entry direction at the first end 16 to a substantially horizontal exit direction at the second end 18. The change in direction from the first end 16 to the second end 18 has an angle of approximately 120° to 60°. However, it is noted that any angle between 0° and 180° may be used to supply the gas to the main conduit outlet portion 14 in a substantially forward direction 22. In the illustrated embodiment, the first end 16 of the gas conduit is located between the inlet portion 12 and outlet portion 14 of the main conduit. The second end 18 of the gas conduit is adjacent the outlet portion 14 of the main conduit. The gas conduit 20 is adapted to direct the delivered gas towards the outlet portion 14 of the main conduit such that the second gas enters the main conduit in a forward direction as indicated by arrow 22.

The gas conduit 20 has a diameter large enough to allow sufficient gas flow and to minimize noise, for example 3 mm to 10 mm in diameter. As mentioned above, the diameter of the gas conduit at the entry of the first end 16 may be smaller than the diameter of the gas conduit at the exit of the second end 18. For example the first end 16 diameter may be in the range of 2 to 10 mm, e.g., 4-7 mm, and the diameter of the second end 18 may be in the range of 3 to 12 mm, e.g., 5-8 mm. The overall size and shape of the connector 10 may vary according to the desired application.

As seen in FIG. 2, the second end 18 of the gas conduit 20 protrudes into the main conduit such that the inner diameter of the main conduit is smaller at the outlet portion 14 than at the inlet portion 12. That is, the main conduit transitions from a larger cross-section at the inlet portion 12 to a smaller cross-section at the outlet portion 14. This design provides a uniform wall thickness for the connector and facilitates the use of standard ISO conic connection ends for both ends of the connector. Alternatively, the inner diameter of the main conduit may be substantially constant and the inner conduit 18 results in a larger outer diameter for the outlet portion 14.

The supplied gas accelerates as it bends around the angle between the first end 16 and the second end 18 of the gas conduit. The second end 18 of the gas conduit 20 has a tapered shape such that the exit end has a larger diameter than the entry end. The tapered shape may be produced by the inner wall of the second end 18 of the gas conduit 20 having a tapered angle. The tapered angle may be in the range of 0° to 20°, e.g., 2° to 7°. The tapered angle assists in smoothing the flow of the gas following the gas acceleration as a result of the change in direction required by the gas when it travels from the first end 16 of the gas conduit to the second end 18 of the gas conduit. The diameter of the second end 18 of the gas conduit 20 assists in determining the level of mixing between the pressurized first gas and the second gas.

In an embodiment, the internal diameter along the gas conduit 20 may be selected to reduce the flow velocity at the bend or elbow between the first and second ends 16, 18, e.g., to reduce the risk of ignition from friction.

The gas conduit 20 directs the supply of the second gas in the forward direction only (indicated by arrows 22 and 24) such that even if the PAP device is turned off the second gas supplied will continue to flow towards the outlet portion 14 of the connector such that the second gas is substantially prevented from flowing back towards the inlet portion 12 of the main conduit. The supply of pressurized second gas through the gas conduit 20 and into the main conduit outlet portion 14 facilitates a Venturi effect. The second gas is accelerated to a higher flow velocity than the first gas when entering the main conduit in the forward direction. The higher, always forward flow, velocity of the second gas, when interacting with the zero or lower flow velocity of the first gas, can develop a negative differential pressure boundary, resulting in the net forward volumetric flow of the first gas.

The higher velocity second gas stream traveling through the gas conduit 20 and into the outlet portion 14 of the main conduit produces a lower pressure boundary in the main conduit, which generates the Venturi effect. The lower pressure boundary results in a net negative pressure causing the first gas to flow forward at the inlet of the main conduit. This is similar to a Bunsen burner effect. This design also advantageously facilitates the mixing of the second gas with the first gas flowing in the main conduit. This Venturi effect also facilitates purging of any second gas remaining in the system from previous use when the device is initially turned on.

Figure 5:
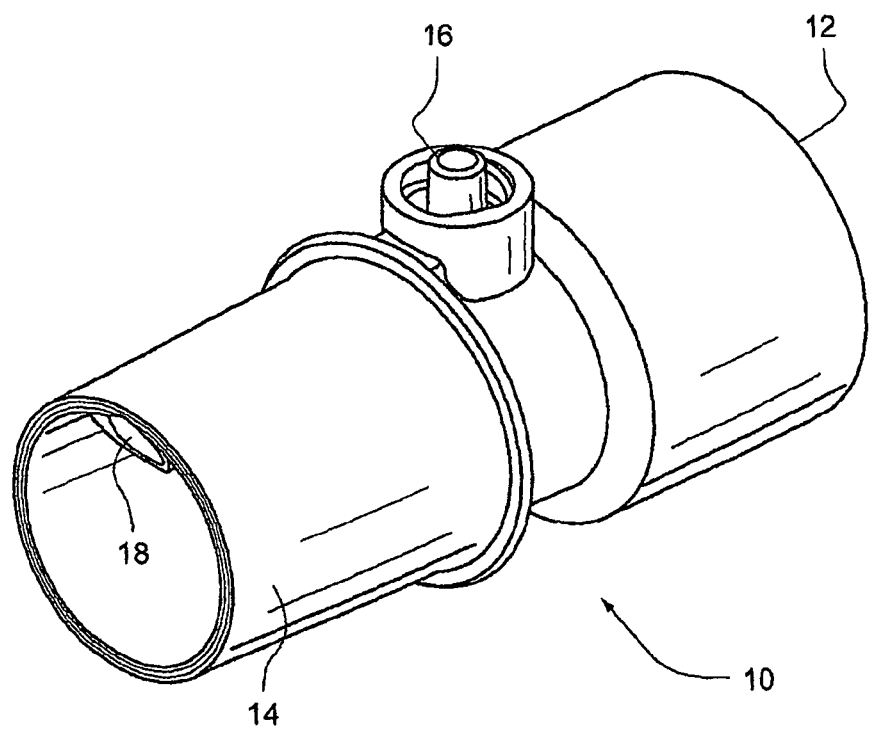
FIG. 5 shows an alternative embodiment of the connector having a Luerlock connector.

A second gas supply system is attached to the entry end 16 of the gas conduit 20 using any known connection mechanism such as screw, leurlock (see FIG. 5), snap on, clamp or similar connections. The second gas is preferably supplied via a tube connected to the second gas source. Generally gases such as oxygen are supplied in cylinders or from an outlet in a wall. The connector 10 may be made from any suitable material having a high auto ignition temperature, such as polycarbonate, polysulphon or polyetherimide. In an embodiment, the connector may be made by injection molding. The connector may be made to fit to any tubing diameter and preferably fits to any standard respiratory tubing and PAP device known in the art.

Figure 4:
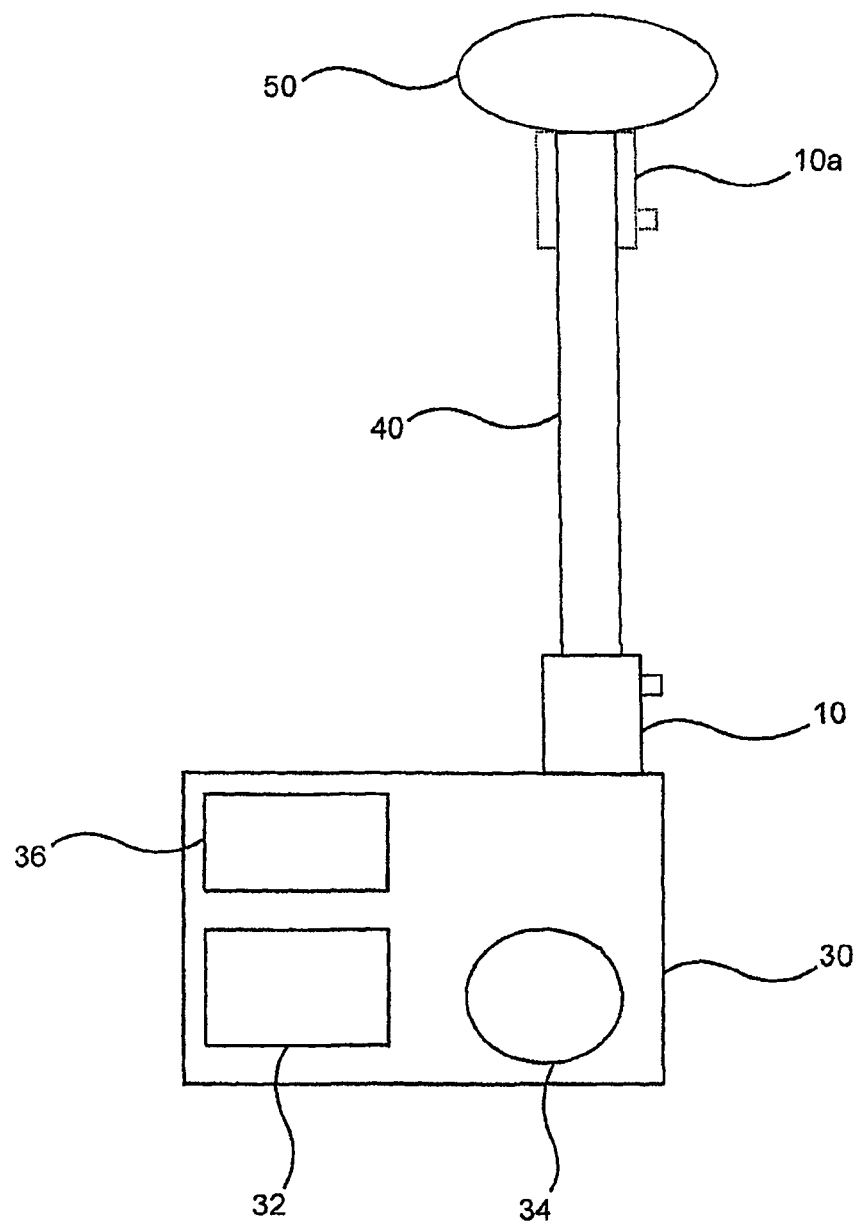
FIG. 4 shows a respiratory system comprising a connector according to an embodiment of the invention.

FIG. 4 shows a respiratory system including a connector 10 according to an embodiment of the invention. A PAP device 30 includes a motor 34 that provides a supply of pressurized air for the administration of CPAP treatment. The pressurized air is delivered to a patient via a patient interface 50. An air delivery conduit 40 is coupled between the PAP device 30 and the patient interface 50. The PAP device may comprise a user interface unit 32 to allow information input and a display unit 36 to display output information. The connector 10 may be attached between the PAP device 30 and the air delivery conduit 40 as shown or between the air delivery conduit 40 and the patient interface 50 as indicated by the dotted connector 10a.

When a humidifier is attached to the respiratory system, the connector 10 may be placed between the PAP device and the humidifier. Alternatively, the connector 10 may be placed after (downstream of) the PAP device and the humidifier.

In one embodiment, the respiratory system may also comprise a sensor to monitor the concentration of gas entering the system. A sensor, such as an oxygen sensor, may be located within the connector or within the respiratory device.

The connector 10 may be a separate component for attachment in the respiratory system or be integrally formed as part of a component of the respiratory system, for example as part of the air outlet of the PAP device 30, as part of the patient interface unit 50 or as part of the air delivery conduit 40.

The patient interface 50 may have any suitable configuration as is known in the art, e.g., full-face mask, nasal mask, oro-nasal mask, mouth mask, nasal prongs, etc. The invention encompasses the use of both vented and non-vented masks and single or dual tube breathing gas supply systems.

FIGS. 6-1 to 6-12 illustrate a connector 210 according to another embodiment of the present invention. In this embodiment, the connector 210 includes a gas conduit 220 structured to direct a second gas (e.g., oxygen) into a center of the gas flow path.

As illustrated, the connector 210 includes a main conduit having an inlet portion 212 and an outlet portion 214 that form a passage for supply of a first gas. The inlet portion 212 is adapted to receive a supply of a first gas and deliver the first gas to the outlet portion 214 as indicated by arrows 222 and 224 (e.g., see FIGS. 6-10 to 6-12). The connector 210 further comprises a gas conduit 220 (or supplemental conduit) having a first end 216 and a second end 218 that form a second passage for supply of a second gas.

In the illustrated embodiment, the gas conduit 220 has a generally L-shape with the first end 216 sloped with respect to the second end 218, e.g., angle α between about 90° to 135°, e.g., 120° (see FIG. 6-10). However, other suitable angles between the first and second ends 216, 218 may be used, e.g., between 0° and 180°. In use, supplied gas is directed from the first end 216 to a substantially horizontal exit direction at the second end 218.

In the illustrated embodiment, the first end 216 of the gas conduit 220 is located between the inlet portion 212 and outlet portion 214 of the main conduit, and the second end 218 of the gas conduit 220 is adjacent the outlet portion 214 of the main conduit. The gas conduit 220 is adapted to direct the delivered gas towards the outlet portion 214 of the main conduit such that the second gas enters the main conduit in a forward direction as indicated by arrow 222. Moreover, the second end 218 delivers the second gas into a center of the main conduit (e.g., along the axis of the main conduit) such that delivery of the second gas is symmetric to help reduce impedance and mixing with the pressurized air.

As illustrated, a plurality of fins or wings 225 support the second end 218 within the center of the main conduit. One of the fins 225 forms a portion of the first end 216, i.e., the portion of the first end that extends into the main conduit and interconnects with the second end. In FIGS. 6-1, 6-2, 6-8, and 6-9, the connector 210 includes three fins 225 regularly spaced and separated from one another within the main conduit. Such three fin arrangement may be advantageous from a tooling perspective as it may help to maintain the circular shape of the gas conduit passage. However, the connector 210 may include any suitable number of fins, e.g., 1, 2, 3, or more fins.

Figures 1, 6:
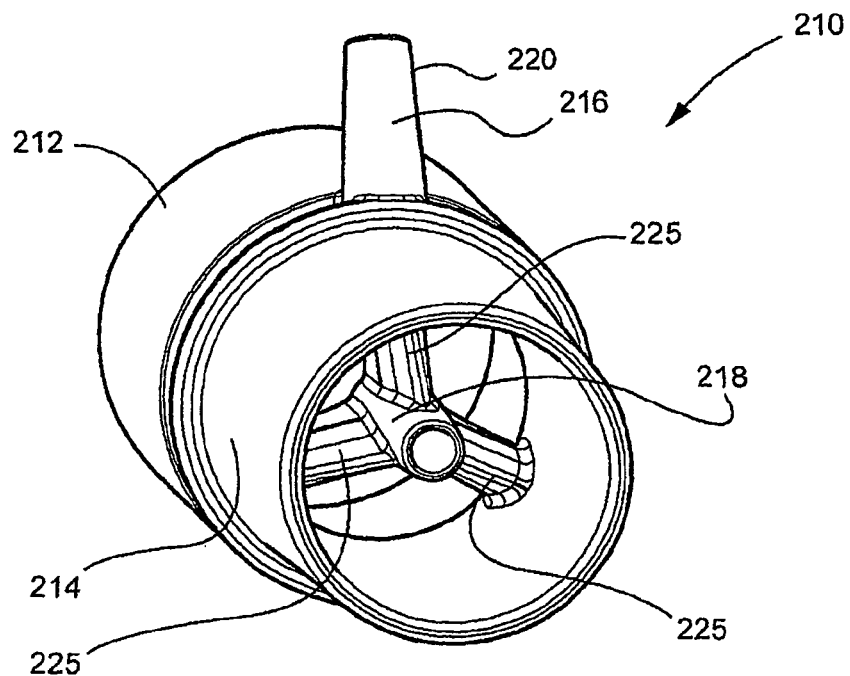
Figures 2, 6:
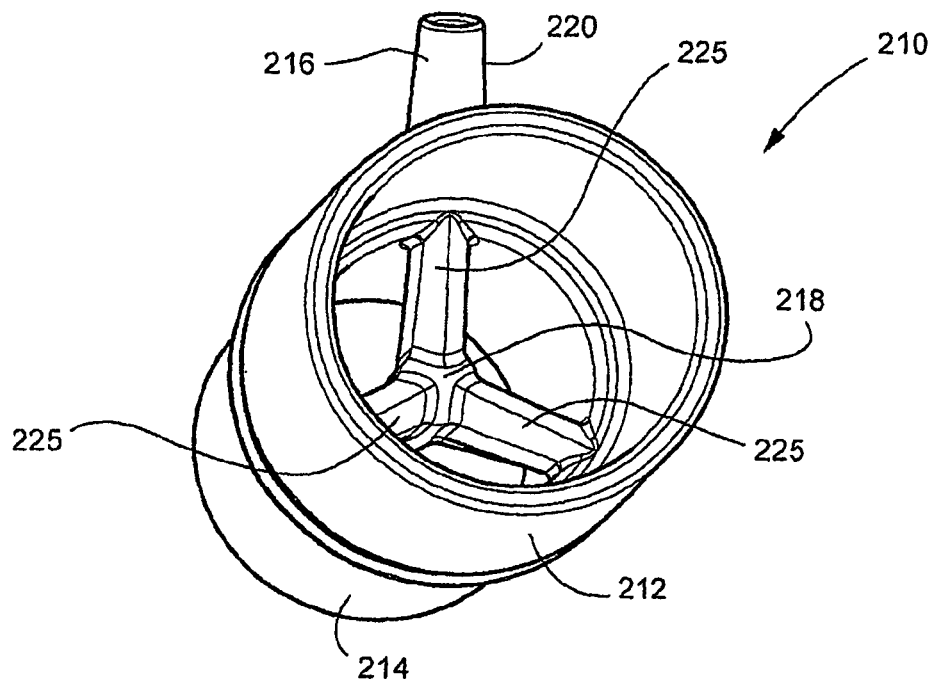
Figures 3, 6:
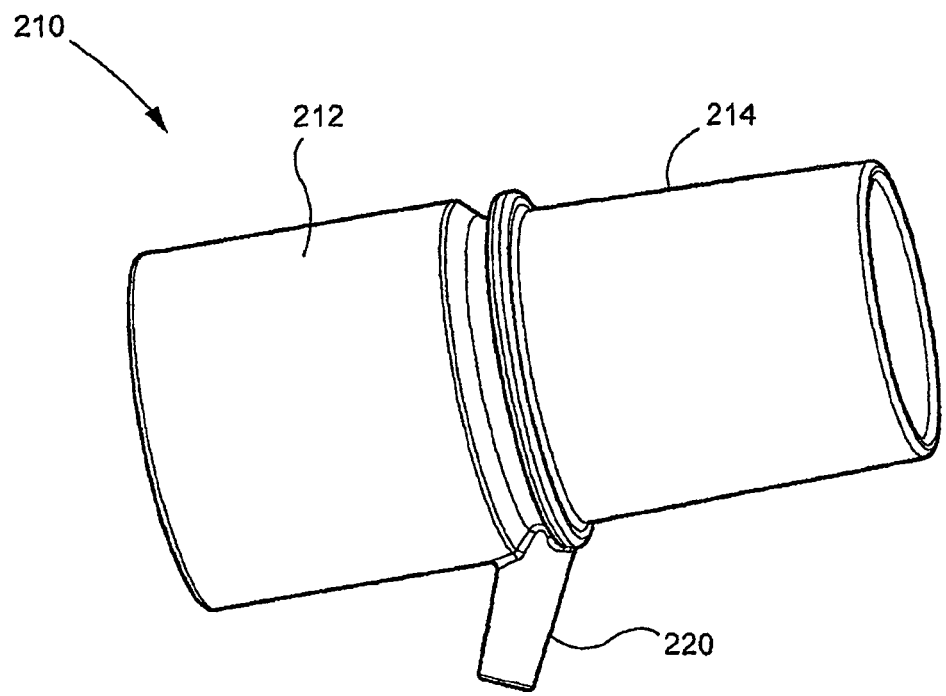
Figures 4, 6:
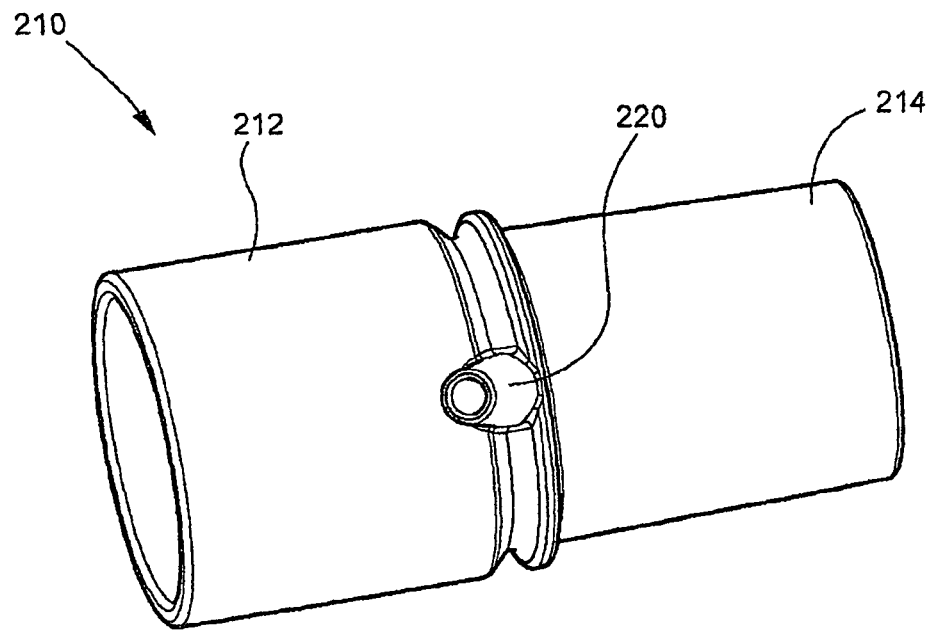
Figures 5, 6:
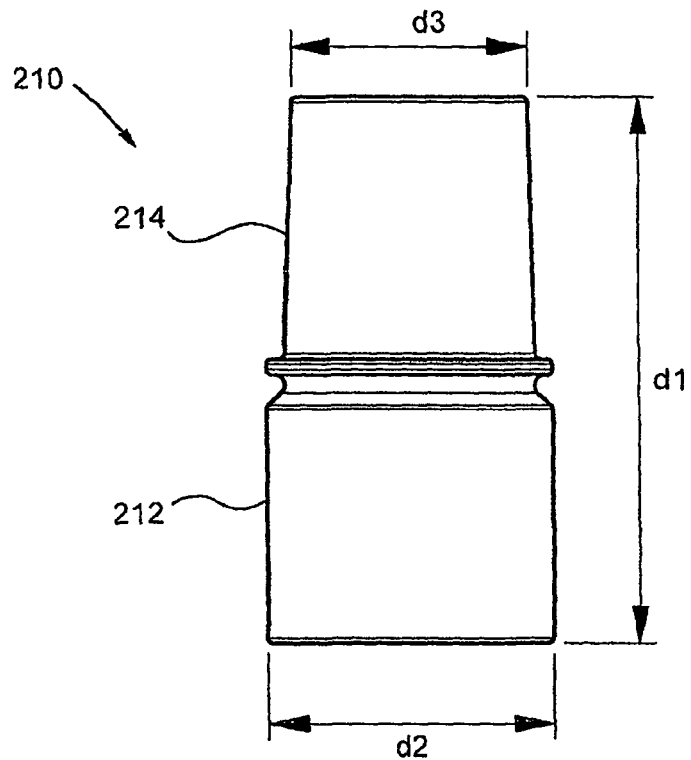
Figure 6:
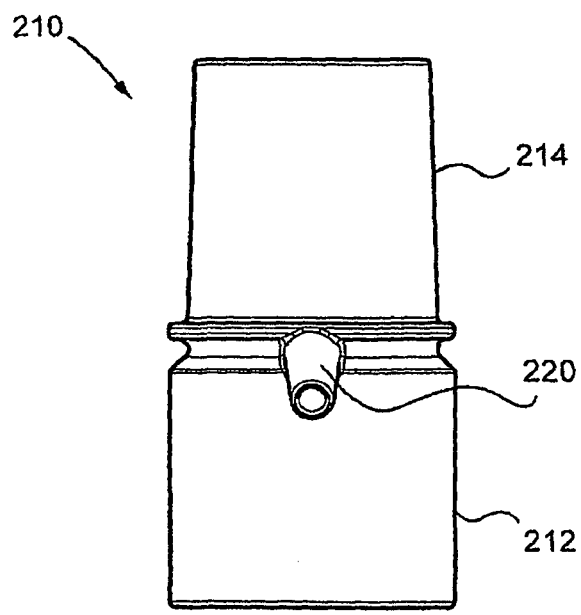
Figures 6, 7:
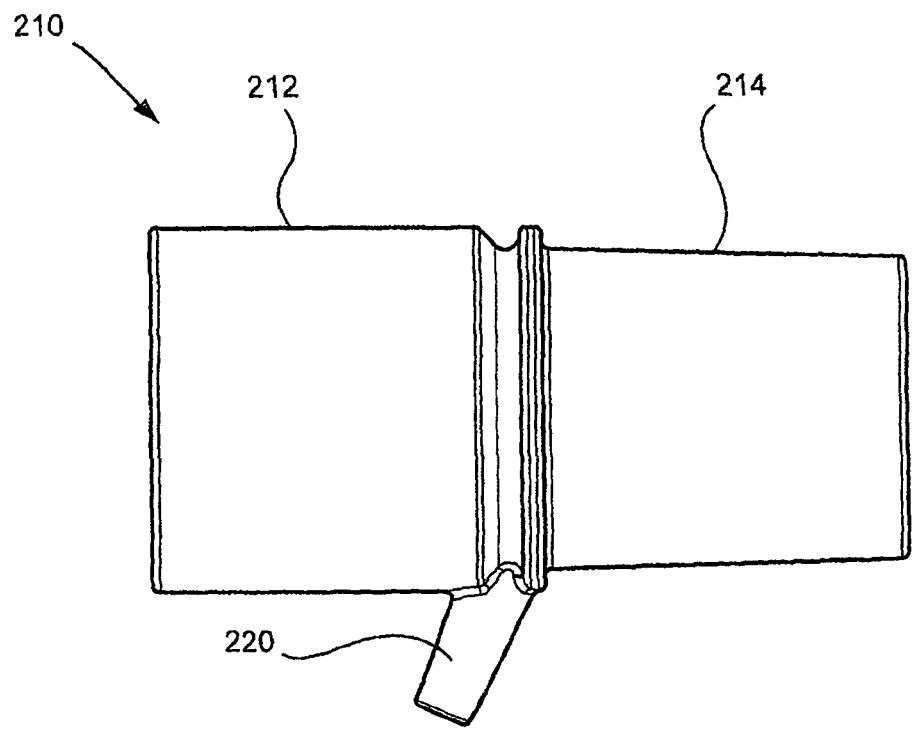
Figures 6, 7, 8:
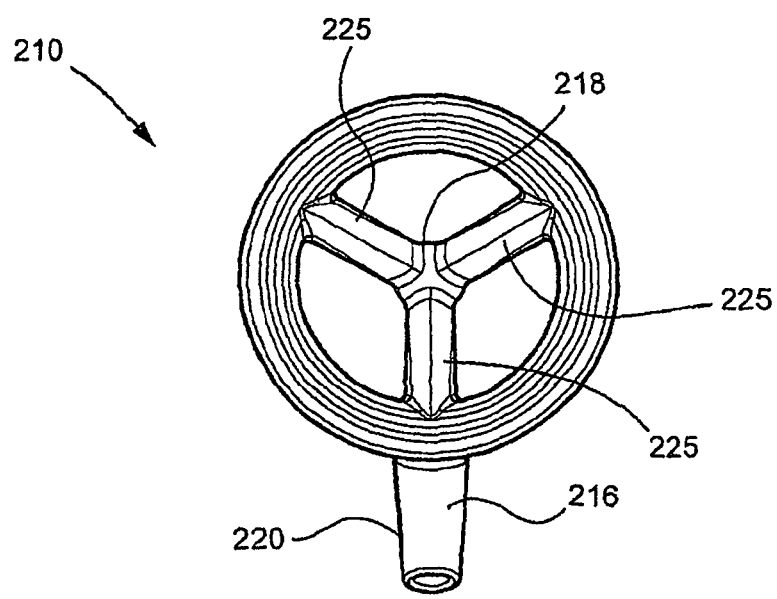
Figures 6, 7, 8, 9:
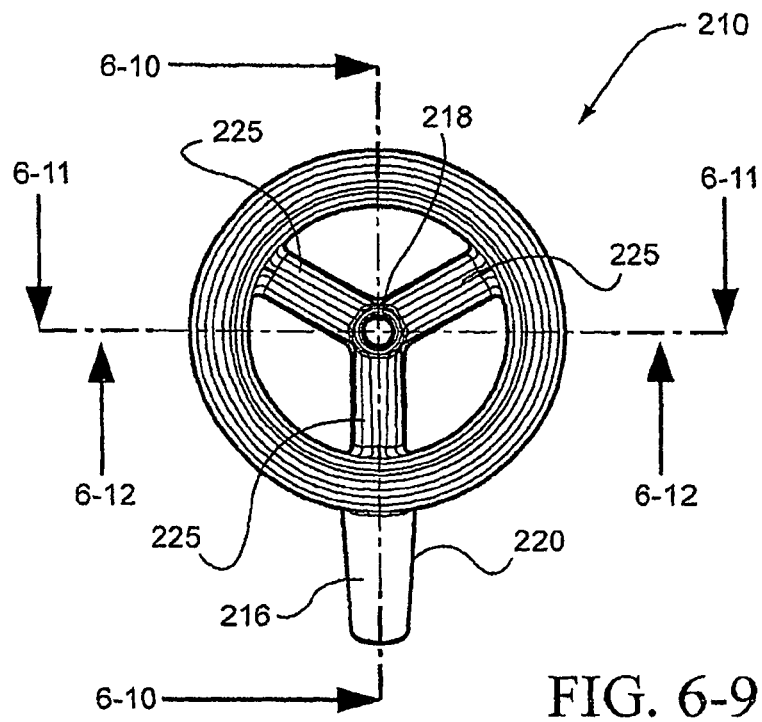

For example, FIGS. 8-1 and 8-2 illustrate a connector 310 including a gas conduit 320 having a first end 316 and a second end 318 supported by a single fin 325. Also, FIG. 9 illustrates a connector 410 including a gas conduit 420 having a first end 416 and a second end 418 supported by two fins 425 diametrically opposed from one another. However, other suitable fin arrangements are possible, e.g., fins irregularly spaced and separated from one another within the main conduit.

Figures 6, 7, 8, 9, 10:
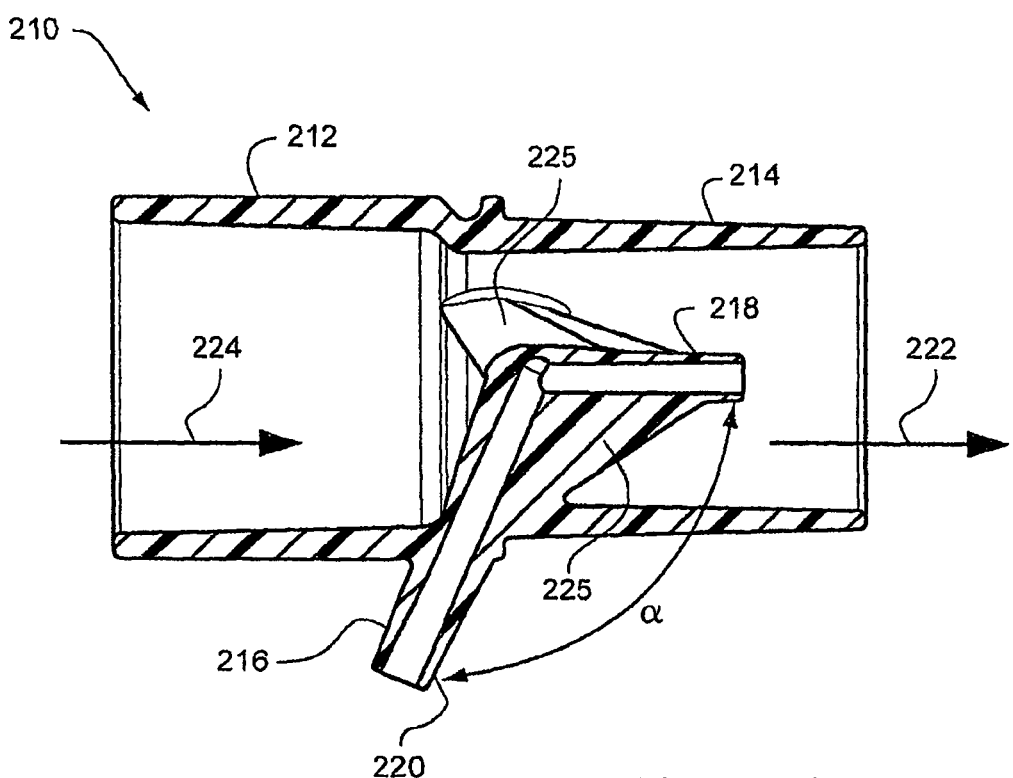

In the illustrated embodiments, each fin 225 is aerodynamically designed to reduce impedance and turbulence in the air path. In addition, each fin 225 is designed to encourage a smooth flow of gas and oxygen down the air path. FIGS. 10-1 and 10-2 are exemplary views of a fin 225 showing the contoured exterior surface 226. However, it should be appreciated that fins of different shapes may be used.

The gas conduit 220 has a diameter large enough to allow sufficient gas flow and to minimize noise, e.g., 2 mm to 10 mm in diameter. In an embodiment, the diameter of the gas conduit at the entry of the first end 216 may be smaller than the diameter of the gas conduit at the exit of the second end 218. Alternatively, the first and second ends 216, 218 may be substantially similar in diameter. For example, the first end 216 diameter may be in the range of 2 to 10 mm, e.g., 2.6 mm, and the diameter of the second end 218 may be in the range of 2 to 12 mm, e.g., 2.8 mm. However, it is to be understood that these dimensions and ranges are merely exemplary and other dimensions and ranges are possible depending on application.

In an embodiment, the connector 210 may have a length d1 of about 50-60 mm (e.g., 52 mm), a diameter d2 at the inlet portion 212 of about 20-30 mm (e.g., 26 mm), and a diameter d3 at the outlet portion 214 of about 15-25 mm (e.g., 21.6 mm). The interior surface of the inlet portion 212 may be tapered to facilitate connection, and the exterior surface of the outlet portion 214 may be tapered to facilitate connection.

As described above, the connector 210 may use a Venturi effect to increase the air flow to envelope the oxygen flow in a centralized flow. That is, the higher velocity second gas stream traveling through the gas conduit 220 and into the outlet portion 214 of the main conduit produces a lower pressure boundary in the main conduit, which generates the Venturi effect.

In an embodiment, the connector 210 is molded from polycarbonate to provide a durable, low cost part. However, the connector may be formed in other suitable manners with other suitable materials. In an embodiment, a high gloss finish may be provided to the internal surface and/or external surface of the connector.

FIG. 7 is a perspective view illustrating the connector 210 attached to the outlet of a PAP device 230 adapted to provide a supply of pressurized air for CPAP treatment. It should be appreciated that the connector 230 may be suitably sized to fit to any suitable PAP device and/or respiratory tubing as known in the art.

Figures 6, 7, 8, 9, 10, 11:
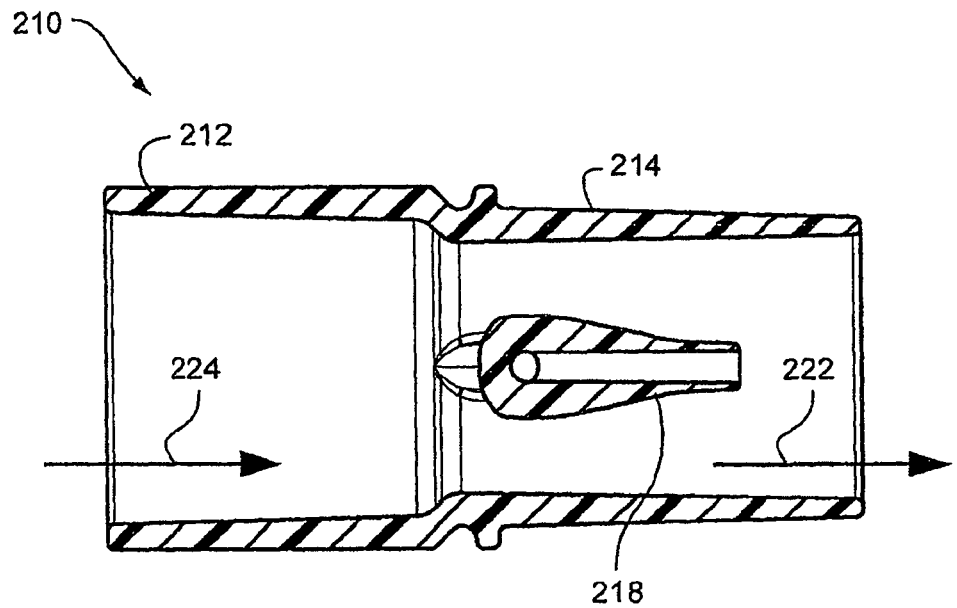
Figures 6, 7, 8, 9, 10, 11, 12:
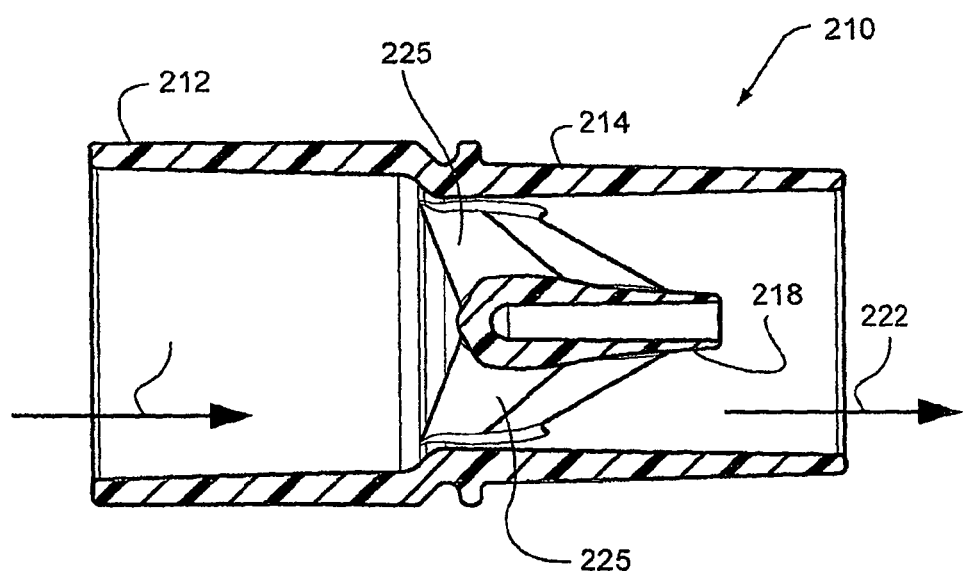
Figure 7:
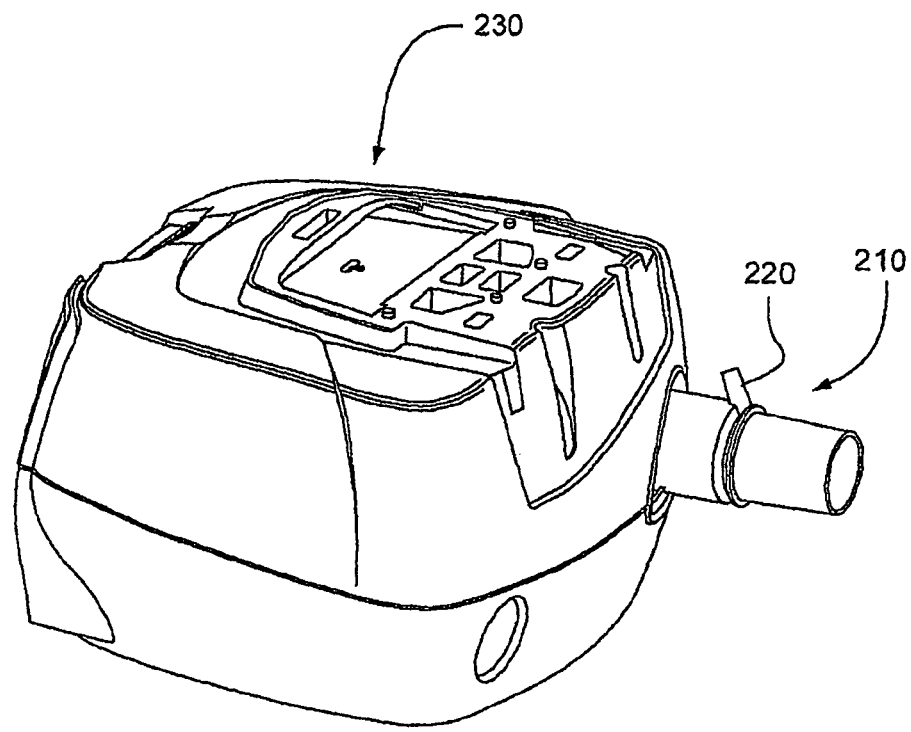
Figures 1, 8:
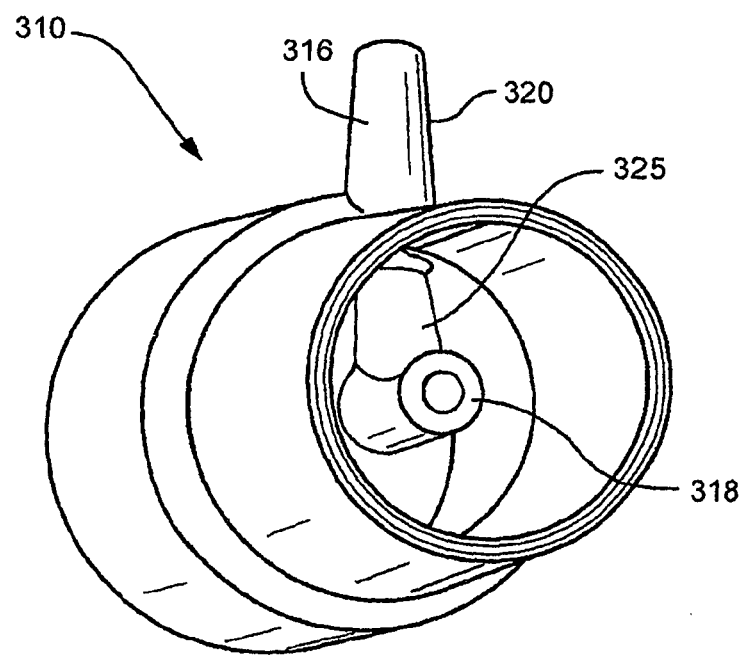
Figures 2, 8:
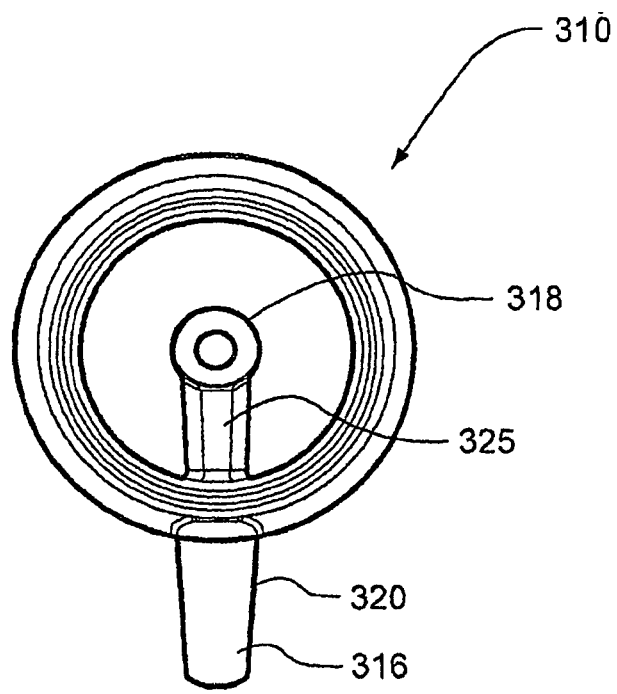
Figure 9:
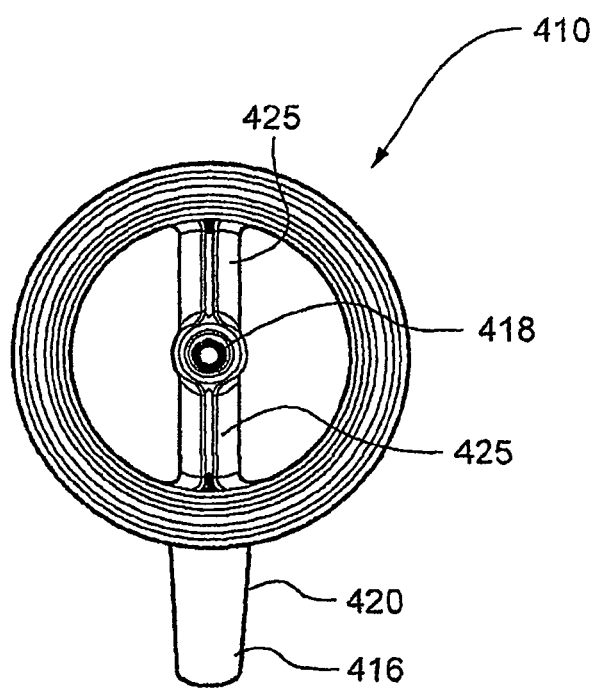
Figures 1, 10:
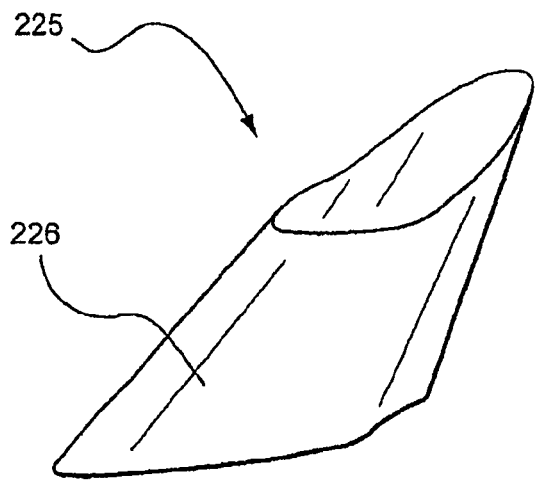
Figures 2, 10:
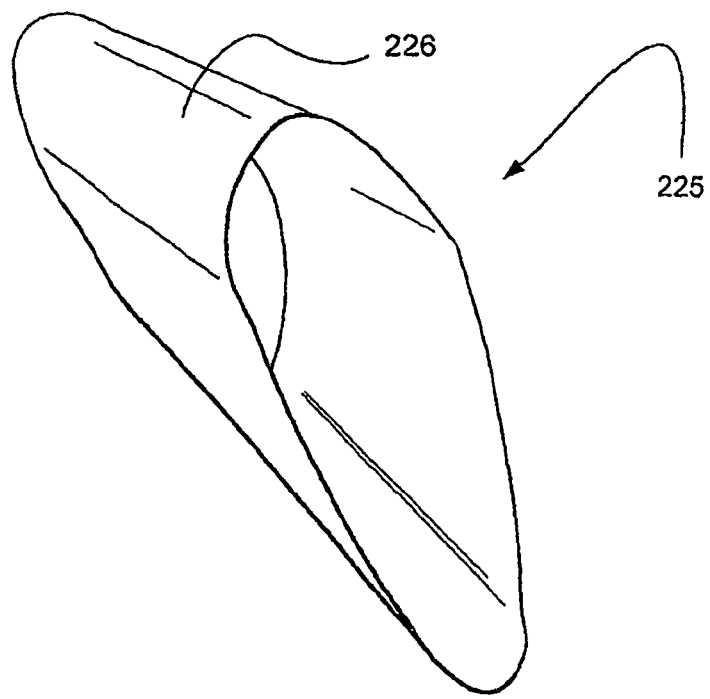
Figures 1, 11:
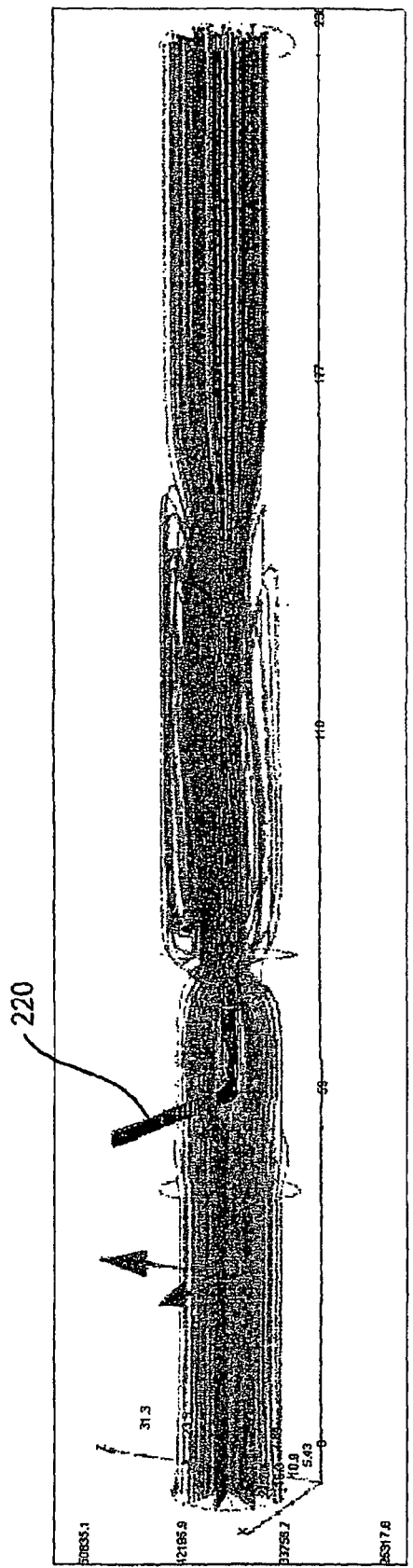
Figures 2, 11:
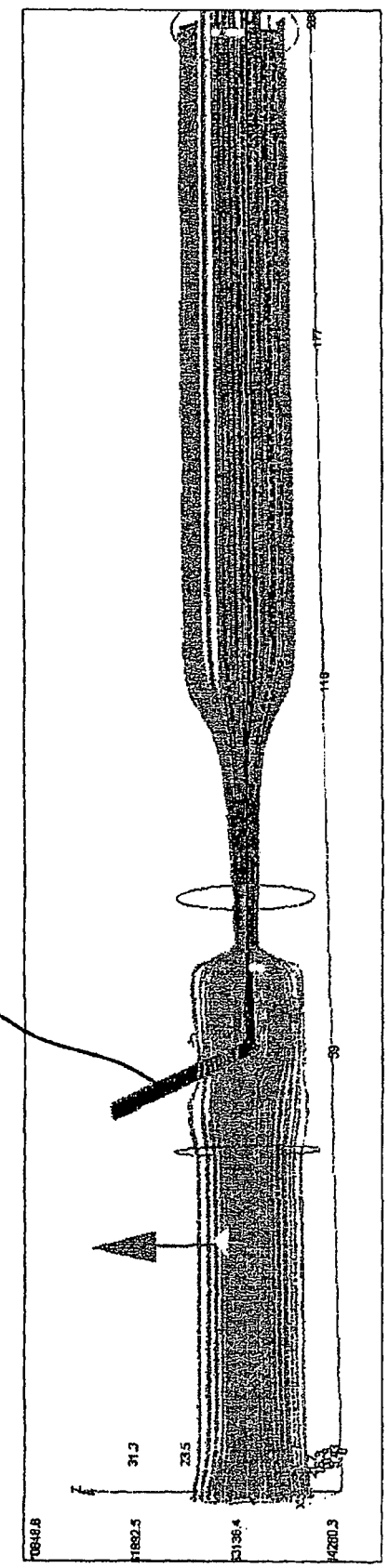

FIG. 11-1 illustrates flow through the connector 210 at high pressure from the PAP device (20 cmH2O), and FIG. 11-2 illustrates flow through the connector 210 at high oxygen flow from the gas conduit 220 (15 L/min). Regardless of the flow from the PAP device, the oxygen flow is enveloped in the PAP device flow and is centralized as it flows up the tube. In addition, due to the internal structural design, there is minimal turbulence from the oxygen entering the airflow. Further, the gas conduit 220 reduces backflow (e.g., oxygen flow back) to the PAP device to a much higher level, especially at higher oxygen flow and lower CPAP pressures.

The connector according to embodiments of the invention advantageously provides for the safe mixing of a first gas, such as air, with a second gas, such as oxygen. The second gas is safely prevented from accumulating to high levels within a respiratory device when the respiratory device is inactive, for example when the respiratory device is turned off. In addition the connector according to embodiments of the invention is easy to use and attach to a respiratory device, humidifier, air delivery tubing and/or mask.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A connector comprising:
   a main conduit having an inlet portion and an outlet portion that form a first passage for supply of a first gas in a forward direction, the inlet portion is adapted to receive a supply of the first gas and deliver the first gas to the outlet portion;
   a gas conduit having a first end and a second end that form a second passage for supply of a second gas, the first end of the gas conduit is adapted to connect to a second gas supply, and the second end is adjacent the outlet portion of the main conduit and delivers the second gas into the main conduit such that the second gas is directed to flow in the forward direction to facilitate mixing of the second gas with the first gas in the main conduit.

2. The connector according to claim 1, wherein the second gas is accelerated to a higher velocity than the first gas when entering the main conduit in the forward direction.

3. The connector according to claim 1, wherein a negative differential pressure boundary is created between the second gas and the first gas such that the first gas is directed to flow in a net forward direction.

4. The connector according to claim 1, wherein the inner diameter of the inlet portion of the main conduit is larger than the inner diameter of outlet portion of the main conduit.

5. The connector according to claim 1, wherein at least part of the gas conduit is within the main conduit resulting in a reduced inner diameter of the outlet portion of the main conduit compared to the inlet portion of the main conduit.

6. The connector according to claim 1, wherein the gas conduit is tapered from the second end to the first end.

7. The connector according to claim 1, wherein the second gas is substantially prevented from flowing towards the inlet portion of the main conduit.

8. The connector according to claim 1, wherein the connector is injection molded.

9. The connector according to claim 8, wherein the connector is made from polycarbonate, polysulphon, polyetherimide or any other suitable oxygen compatible material with a high auto ignition temperature.

10. A connector adapted to provide supplemental gas to a respiratory system comprising:
a main conduit having an inlet portion and an outlet portion that form a first passage for supply of a first gas in a forward direction, the inlet portion is adapted to receive a supply of the first gas and deliver the first gas to the outlet portion;
a gas conduit having a first end and a second end that form a second passage for supply of a second gas, the first end of the gas conduit is adapted to connect to a second gas supply, and the second end is adjacent the outlet portion of the main conduit and delivers the second gas into the main conduit such that the second gas is directed to flow in the forward direction,
wherein the second end of the gas conduit has a tapered shape such that a diameter at an exit of the second end is larger than a diameter at an entry of the second end.

11. A respiratory system comprising a positive air pressure (PAP) device, a patient interface unit, an air delivery conduit, and a connector according to claim 1.

12. The respiratory system according to claim 11, wherein the connector is integrally formed with one of the PAP device, patient interface unit or the air delivery conduit.

13. The respiratory system according to claim 12, wherein the connector is integrally formed as part of the outlet of the PAP device.

14. The connector according to claim 1, wherein a diameter of the gas conduit at an entry of the first end is smaller than a diameter of the gas conduit at an exit of the second end.

15. The connector according to claim 1, wherein the second end of the gas conduit has a tapered shape such that a diameter at an exit of the second end is larger than a diameter at an entry of the second end.

16. The connector according to claim 1, wherein the second gas is accelerated to a higher flow velocity than the first gas when entering the main conduit in the forward direction.

17. The connector according to claim 1, wherein the second end is positioned and arranged to direct the second gas into a center of the first passage.

18. The connector according to claim 17, wherein the gas conduit has a generally L-shape.

19. The connector according to claim 18, wherein the first and second ends form an angle of about 90-135° therebetween.

20. The connector according to claim 17, wherein the second end is adjacent the outlet portion of the main conduit.

21. The connector according to claim 17, wherein the second end is positioned and arranged to direct the second gas along the axis of the main conduit.

22. The connector according to claim 17, further comprising one or more fins to support the second end within the center of the first passage.

23. The connector according to claim 22, wherein the second end is supported by three fins regularly spaced and separated from one another within the main conduit.

24. The connector according to claim 22, wherein each fin is aerodynamically designed to reduce impedance and turbulence in the first passage.

25. A respiratory system comprising a PAP device, a patient interface unit, an air delivery conduit, and a connector according claim 17.

* * * * *